(12) United States Patent
Wolfe et al.

(10) Patent No.: US 7,574,264 B2
(45) Date of Patent: Aug. 11, 2009

(54) MULTIRATE COCHLEAR STIMULATION STRATEGY AND APPARATUS

(75) Inventors: Joe Wolfe, Coogee (AU); Paul M. Carter, Carlingyard (AU); Robert Fearn, Maroubra (AU); Niki Frampton, Wamberal (AU); Simon G. Parker, Ryde (AU)

(73) Assignee: Cochlear Limited, Lane Cove, NSW (AU)

( * ) Notice: Subject to any disclaimer, the term of this patent is extended or adjusted under 35 U.S.C. 154(b) by 437 days.

(21) Appl. No.: 11/385,677

(22) Filed: Mar. 22, 2006

(65) Prior Publication Data

US 2006/0212095 A1 Sep. 21, 2006

Related U.S. Application Data

(62) Division of application No. 10/030,830, filed as application No. PCT/AU00/00838 on Jul. 12, 2000, now Pat. No. 7,072,717.

(30) Foreign Application Priority Data

Jul. 13, 1999 (AU) .................... PQ1610

(51) Int. Cl.
*A61N 1/18* (2006.01)
(52) U.S. Cl. .............. 607/57; 381/12; 381/20; 607/55; 607/56; 607/137
(58) Field of Classification Search ........... 607/55, 607/56, 57, 72, 137; 381/12, 20
See application file for complete search history.

(56) References Cited

U.S. PATENT DOCUMENTS

| 3,125,723 | A | * | 3/1964 | Spogen ............... 704/213 |
| 3,535,454 | A | * | 10/1970 | Miller ............... 704/268 |
| 3,546,584 | A | * | 12/1970 | Alister ............... 324/76.15 |
| 3,629,510 | A | * | 12/1971 | Anderson et al. ........ 704/208 |
| 4,357,497 | A | | 11/1982 | Hochmair et al. |
| 4,400,590 | A | | 8/1983 | Michelson |
| 4,441,202 | A | | 4/1984 | Tong et al. |
| 4,515,158 | A | * | 5/1985 | Patrick et al. .......... 607/57 |
| 4,532,930 | A | | 8/1985 | Crosby et al. |
| 4,593,696 | A | | 6/1986 | Hochmair et al. |
| 4,611,598 | A | * | 9/1986 | Hortmann et al. ........ 607/57 |
| 4,813,417 | A | * | 3/1989 | Soli et al. ............. 607/56 |
| 5,597,380 | A | | 1/1997 | McDermott et al. |

(Continued)

OTHER PUBLICATIONS

PCT International Search Report for PCT/AU00/00838; filed Jul. 13, 2000; published Jan. 18, 2001 (WO 01/03622 A1).

(Continued)

*Primary Examiner*—Carl H Layno
*Assistant Examiner*—Jennifer Stewart
(74) *Attorney, Agent, or Firm*—Connolly Bove Lodge & Hutz LLP

(57) ABSTRACT

A cochlear implant system in which information about the periodicity of a received audio signal in each filter channel is used as a factor in determining the rate of stimulation applied to a tonotopically placed electrode corresponding to the relevant filter channel. As such, the stimulation rate for each electrode is related to the periodicity of the signal in the filter channel corresponding to that electrode. This may allow for improved perception of pitch by the implant recipient.

24 Claims, 6 Drawing Sheets

U.S. PATENT DOCUMENTS

| | | |
|---|---|---|
| 5,601,617 A | 2/1997 | Loeb et al. |
| 5,749,912 A | 5/1998 | Zhang et al. |
| 5,800,475 A | 9/1998 | Jules |
| 6,289,247 B1 | 9/2001 | Faltys et al. |

OTHER PUBLICATIONS

Supplementary Partial European Search Report for EP 00 94 1808, dated May 13, 2004.

Technical Manual: The Laura Cochlear Prosthesis, Antwerp Bionic Systems, N.V., 1991.

Peeters, et al., "The Laura Cochlear Implant Programmed with the Continuous Interleaved and Phase-Locked Continuous Interleaved Strategies," Cochlear Implants: New Perspectives. Adv. Otorhinolaryngol. Basel, Karger, 1993, vol. 48, pp. 251-268.

Kong, et al., "Psychophysical Studies Investigating a Place/Rate Speech Coding Strategy for a Multi-Electrode Cochlear Implant," Department of Otolaryngology, The University of Melbourne, A thesis submitted for the degree of Doctor of Philosophy, Jul. 1990.

* cited by examiner

MULTIRATE COCHLEAR STIMULATION STRATEGY AND APPARATUS

CROSS-REFERENCE TO RELATED APPLICATIONS

This application is a divisional application of U.S. patent application Ser. No. 10/030,830, now U.S. Pat. No. 7,072,717, filed Jun. 5, 2002, which is a national stage application of PCT/AU2000/000838 filed Jul. 12, 2000, which claims priority from Australian Provisional Application PQ 1610 filed Jul. 13, 1999. The entire disclosure and contents of the above applications are hereby incorporated by reference herein.

BACKGROUND

1. Field of the Invention

The present invention relates generally to cochlear implant prostheses and, more particularly, to applying stimulation pulses to the neural structures of a cochlea in accordance with a multirate cochlear stimulation strategy.

2. Related Art

Cochlear implant systems (also commonly referred to as cochlear devices, cochlear prostheses, and the like; collectively and generally referred to herein simply as "cochlear implant systems" or "cochlear implants") are used to aid patients (also referenced to as recipients, implantee, wearer, user, and the like) having a hearing deficiency. More particularly, these systems include a microphone receiving ambient sounds and converting the sounds into corresponding electrical signals, signal processing means for processing the electrical signals and generating cochlear stimulating signals and an electrode assembly for applying the cochlea stimulating signals to the cochlea of an implantee. In response to such stimulating signals a perception of corresponding ambient sound is elicited in the implantee.

The inner ear of a normal hearing person includes hair cells which convert the displacement of the ear's basilar membrane in response to sound into nervous impulses. Different parts of the basilar membrane of the normal cochlea are displaced maximally by different frequencies of sound so that low frequency sounds maximally displace apical portions whereas higher frequency sounds cause displacement of more basal portions of the membrane. The nervous system is arranged so that a nervous impulse originating from a hair cell located adjacent an apical area of the membrane is perceived as a low frequency sound whereas a nervous impulse originating from a hair cell located adjacent a more basal position of the membrane is perceived as a higher frequency sound. This mapping of position to pitch is well known in the art as the tonotopic arrangement of the cochlea.

In a dysfunctional ear the hair cells may be damaged or absent so that no nervous impulses are generated. In such cases electrical stimulation impulses must be provided artificially to simulate the nervous activity of the hair cells in order to create a perception of sound.

FIG. 1A is a schematic illustration of a totally implantable cochlear implant. In such cochlear implant devices, ambient sounds are detected by a microphone 103 and a transduced signal is thereby generated, representative of the ambient sound. A processor unit 105 then processes this transduced signal according to one of many strategies, (some of which will be explained further below) and based on this processing stimulation currents are applied between the electrodes of a coupled array. For example, in "monopolar" mode stimulation, stimulation currents may be caused to flow between an electrode of the electrode array 109 and an extracochlear electrode 115. Nervous discharges elicited in the basilar membrane are conveyed to the central nervous system of the wearer by auditory nerve 113.

In the event that the stimulation current flows between an apical electrode (such as electrode 111) and extracochlear electrode 115, then a lower pitched hearing sensation will be perceived by a wearer of the prosthesis than will be the case if stimulation current flows between a basal electrode (such as electrode 107) and extracochlear electrode 115 because of the tonotopic arrangement of the cochlea 101. Further pitch information may be transmitted to the wearer corresponding to the rate at which stimulations are delivered.

In the past designers of cochlear implant stimulation strategies have striven to optimize the intelligibility of spoken words as perceived by the wearer of a cochlear implant.

One of the earliest sound processing and cochlear stimulation strategies is described in U.S. Pat. No. 4,532,930 to the present applicant. In that patent there is taught the use of a filter dedicated to extracting the voice pitch of a speech signal. The periodicity of the voice pitch is used to set the stimulation periodicity for two or three electrodes. A second, and possibly third, channel is analyzed to determine periodicity and amplitude in a selected frequency band.

The periodicity extracted from the second filter, and possibly third filter, is used to select which electrode is stimulated for the second and third channels while the periodicity of stimulation of the channel is determined by the periodicity of the output signal from the first filter.

Another stimulation arrangement is described in U.S. Pat. No. 4,207,441. In that system there are n electrodes each coupled to one of n filters. Each electrode is stimulated once per analysis period, with an intensity corresponding to the amplitude of the corresponding filter channel. The analysis period of this system is predetermined and hence is not related to the signal on the filter outputs.

More recently, in EP 0 745 363 there is described a stimulation system which takes into account the temporal behavior of the cochlea. In one described embodiment a wavelet transformation is used to extract the temporal information with a view to using this information to determine the sequence of stimulation of the electrodes. The purpose of the invention is to improve the temporal resolution in response to a rapidly changing audio spectrum.

A problem commonly experienced by users of the above or other types of conventional cochlear implants featuring the above and other conventional stimulation schemes is that while intelligibility of spoken words is often good, the user's pitch perception is less than optimal. Accordingly, it is an object of the present invention to provide an apparatus and method for use in a multi-channel cochlear implant which will improve a users perception of pitch.

SUMMARY

In one aspect of the present invention, a cochlear implant prosthesis for delivering to a recipient's cochlea stimulation pulses representing a received audio signal is disclosed. The cochlear implant prosthesis comprises: a processor configured to process electrical signals corresponding to the received audio signal to produce a plurality of filtered signals having different center frequencies; a plurality of amplitude detectors each producing a magnitude signal dependent on the magnitude of one of said filtered signals; a plurality of pulse requesters each configured to produce a pulse request signal dependent on a periodicity of one of said filtered signals; a pulse generator configured to produce stimulation pluses at time instants dependent on said pulse request signals, with the magnitude of said stimulation pulses dependent on said magnitude signals; and a plurality of electrodes for delivering said stimulation pulses.

In another aspect of the invention, a method for delivering to a recipient's cochlea stimulation pulses representing a received audio signal is disclosed. The method comprises: processing electrical signals corresponding to the received audio signal to produce a plurality of filtered signals having different center frequencies; producing a plurality of magnitude signals each representative of the magnitude of one of said plurality of filtered signals; producing one or more pulse request signals each depending on a periodicity of one of said plurality of filtered signals; producing stimulation pulses at time instants dependent on said one or more pulse request signals, with a magnitude of said stimulation pulses dependent on said magnitude signals; and delivering said stimulation pulses to the recipient's cochlear.

BRIEF DESCRIPTION OF DRAWINGS

The invention will be described in conjunction with the accompanying drawings, in which.

DETAILED DESCRIPTION

The present invention is generally directed to a cochlear implant system in which information about the periodicity of a received audio signal in each filter channel is used as a factor in determining the rate of stimulation applied to a tonotopically placed electrode corresponding to the relevant filter channel. That is, the stimulation rate for each electrode is related to the periodicity of the signal in the filter channel corresponding to that electrode. This may allow for improved perception of pitch by the implant recipient.

The present invention will be described with reference to a specific implementation. However, it will be appreciated that the present invention can be implemented in various ways, with suitable modifications to suit the cochlear implant system in question.

Figure 1A:
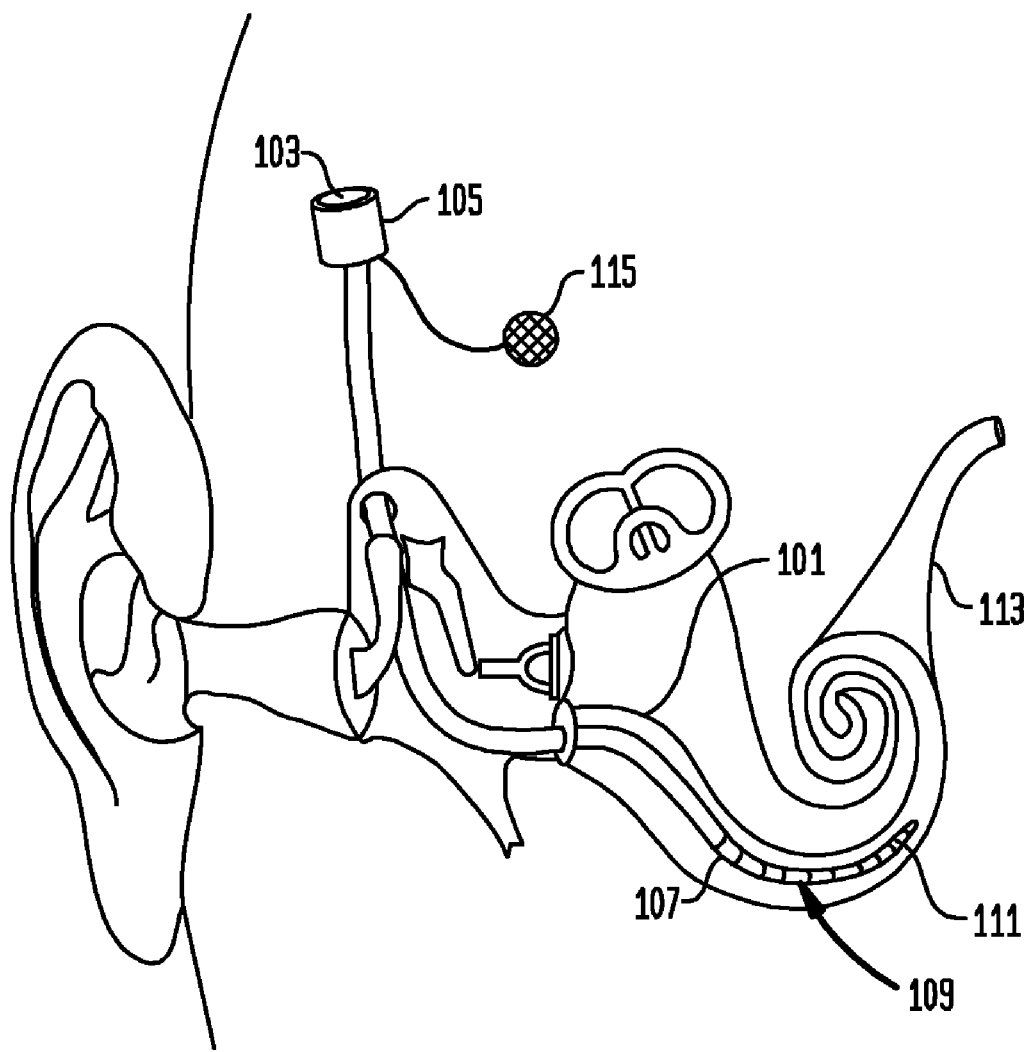
FIG. 1A depicts an exemplary cochlear implant device in which embodiments of the present invention may be advantageously implemented.
Figure 1B:
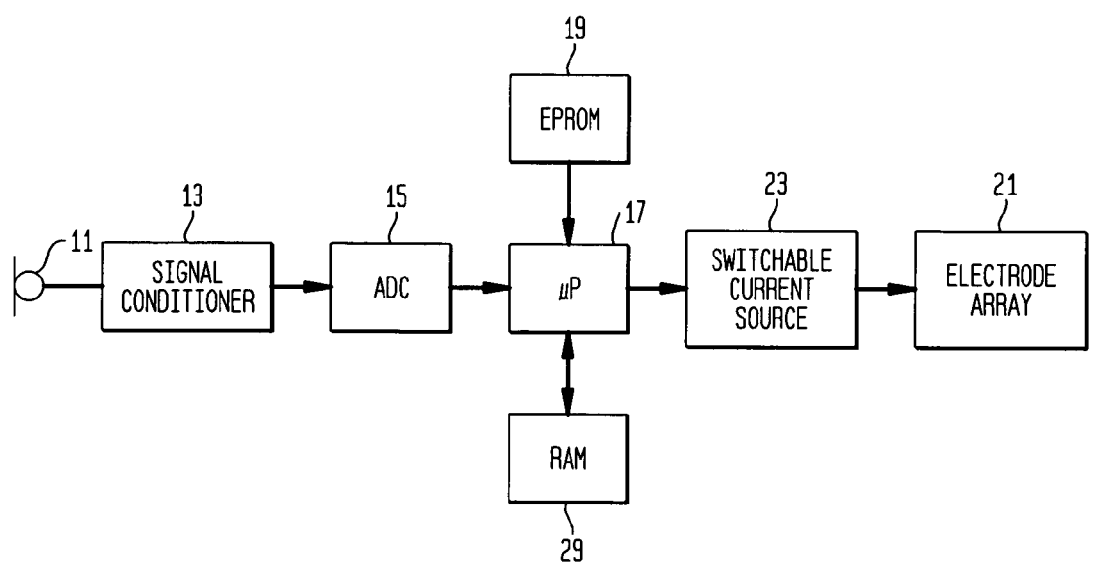
FIG. 1B depicts a block diagram of the primary functional elements of a cochlear implant according to one embodiment of the present invention.

With reference to FIG. 1B, there is depicted a simplified digital hardware implementation of a cochlear prosthesis according to one embodiment of the present invention. Sound waves are transduced by microphone 11 and the electrical produced thereby is processed by a signal conditioning module 13. Signal conditioning module 13 includes standard circuits for pre-amplifying and low pass filtering the signal prior to its processing by analog-to-digital converter ADC 15.

Analog-to-digital converter 15 produces a 16 bit digital signal which is conveyed to microprocessor 17. Microprocessor 17 operates according to a program stored in EPROM 19. Microprocessor 17, in accordance with its executing program, operates upon the digital signal to generate a sequence of stimulation commands which are delivered to a switchable current source module 23. The commands delivered to the switchable current source module 23 specify the amplitude of the current that is to flow from one or more electrodes to one or more other electrodes, the timing of the stimulation current, and the mode of the stimulation. The term 'mode' here refers to the selection of electrodes between which stimulation current is to flow. Well-known stimulation modes include, but are not limited to, bipolar, monopolar and common ground.

Upon receiving commands specifying the parameters of the stimulation to be applied, switchable current source module 23 connects various electrodes of electrode array 21 to an internal controllable current source to generate the appropriate stimulation. The construction of a switchable current source is well-known in the art and may be found in the applicant's U.S. Pat. No. 4,532,930.

Figure 2:
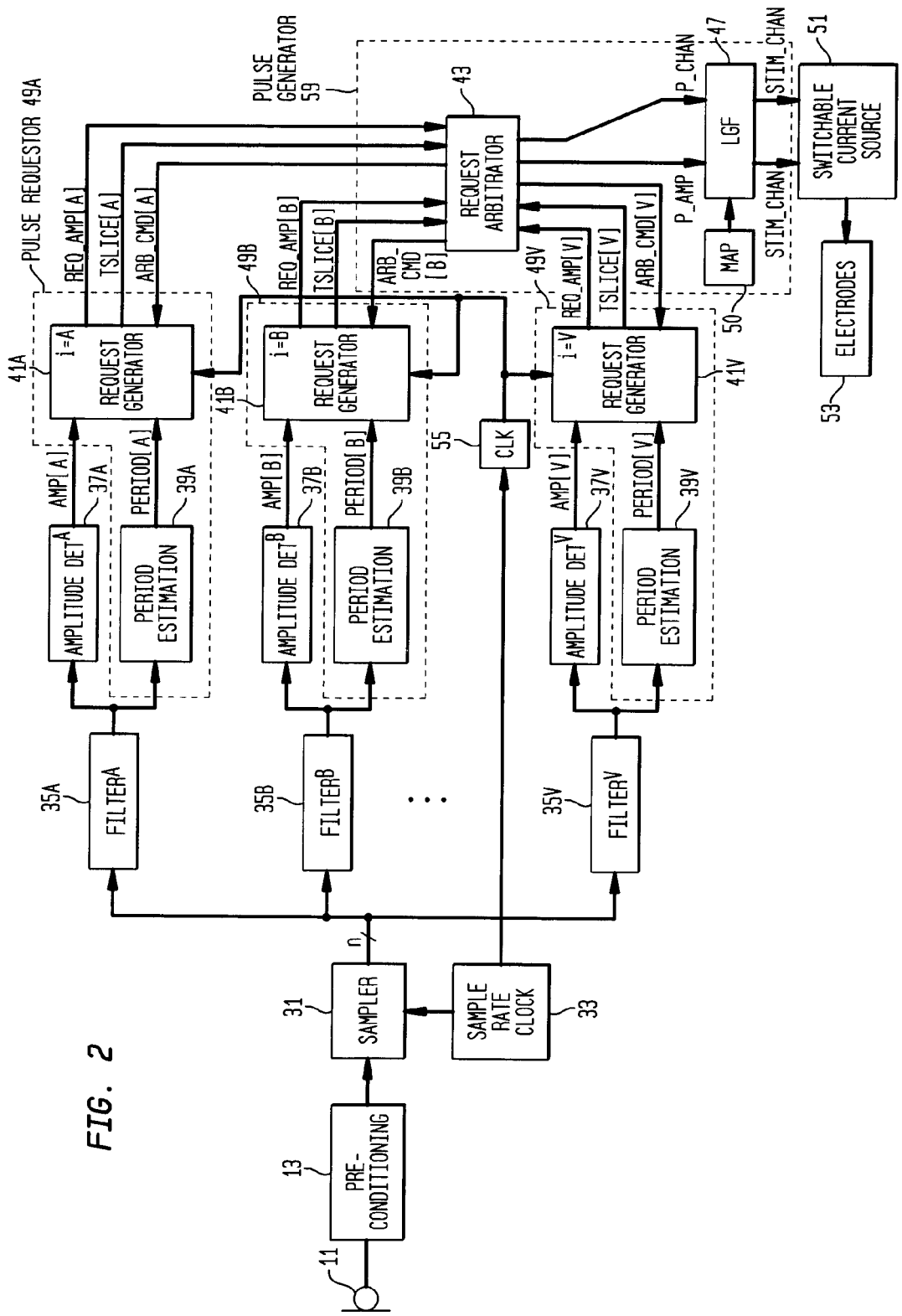
FIG. 2 depicts a dedicated hardware version of a cochlear implant prosthesis according to one embodiment of the present invention.

FIG. 2 depicts a dedicated hardware implementation of one embodiment of the present invention. While FIG. 2 illustrates the invention as if individual tasks performed by microprocessor 17 were embodied in dedicated hardware, it remains the case that the invention is most readily practiced according to the arrangement of FIG. 1B. The invention will, however, be described with reference to FIG. 2 in order to more clearly impart an understanding of the function and its operation of embodiments of the present invention. In the following description, reference will also be made to FIGS. 4 and 5 which are flow charts illustrating the operations performed in certain embodiments of the present invention. FIGS. 3A through 3E are waveforms referred to throughout the following description.

Figure 4:
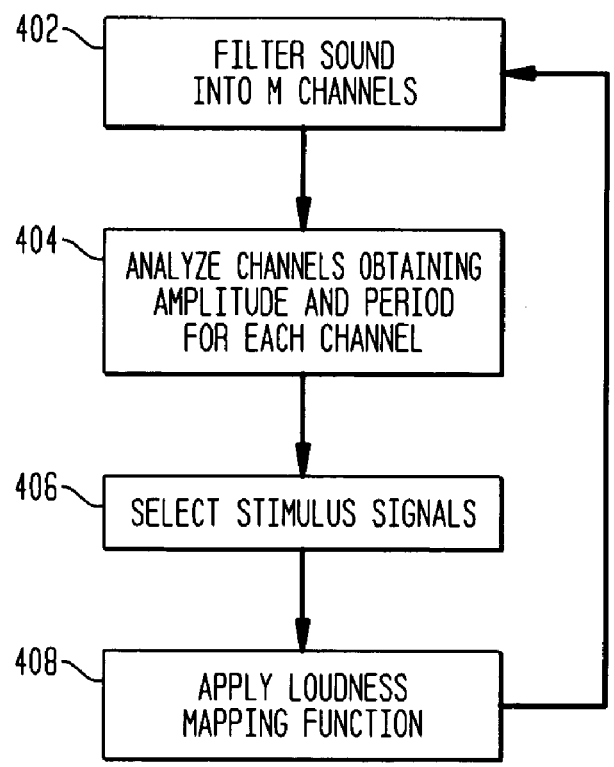
FIG. 4 is a flowchart of operations which may be implemented in embodiments of the present invention by means of software on an apparatus of the type depicted in FIG. 1A.

Referring to FIG. 2 it will be noted that the analog signal from pre-conditioning module 13 is first sampled at 16 kHz by sampler 31 thereby producing a sampled signal. The sampled signal is split 22 ways, each of the split signals providing an input to digital filters 35A-35V which filter the signal into quarter octave frequency bands. It will be appreciated that the numbers of ways the signal is split, and the sampling rate, are matters of design choice appropriate to the system in which the present invention is implemented. Referring to FIG. 4, this operation, described in further detail below, is illustrated in block 402, in which "M" has a value of, in this example, 22.

In one embodiment, digital filters 35A-35V are bandpass and logarithmically spaced with the base frequency being typically at 150 Hz. In one particular embodiment, each filter is of a 6th order Chebychev Type I bandpass type implemented in three second order sections. The quarter octave frequency bands are as shown in Table 1.

TABLE 1

| Filter Band | Lower Frequency Boundary (Hz) | Upper Frequency Boundary (Hz) |
|---|---|---|
| A | 150.00 | 178.38 |
| B | 178.38 | 212.13 |
| C | 212.13 | 252.27 |
| D | 252.27 | 300.00 |
| E | 300.00 | 356.76 |
| F | 356.76 | 424.26 |
| G | 424.26 | 504.54 |
| H | 504.54 | 600.00 |
| I | 600.00 | 713.52 |
| J | 713.52 | 848.53 |
| K | 848.53 | 1009.10 |
| L | 1009.10 | 1200.00 |
| M | 1200.00 | 1427.00 |
| N | 1427.00 | 1697.10 |
| O | 1697.10 | 2018.20 |
| P | 2018.20 | 2400.00 |
| Q | 2400.00 | 2854.10 |
| R | 2854.10 | 3394.10 |
| S | 3394.10 | 4036.30 |
| T | 4036.30 | 4800.00 |
| U | 4800.00 | 5708.20 |
| V | 5708.20 | 6788.20 |

Next, the filter channel signals are analyzed to obtain the amplitude and period for each channel, as depicted at block 404 in FIG. 4. The bandpass filtered signal from each of the digital filters, for example 35A, is provided to an associated amplitude detection module 37A and a period estimation module 39A. The output AMP[A] of amplitude detection module 37A is a digital signal representing an estimation of the amplitude of the sampled signal from filter 35A. The construction of module 37A is straightforward, well understood by those skilled in the art, and will not be explained in further detail herein other than to say that it could be based on a series of comparators.

Period estimation module 39A counts sampling periods between positive zero crossings of the signal from, filter 35A. The output signal PERIOD[A] is scaled so that it is expressed in units of "timeslices".

One "timeslice" is the time taken to deliver one stimulation pulse by means of an electrode. With reference to FIG. 3E an example of a stimulation current pulse waveform comprises a first "phase" 104 being a square wave of predetermined amplitude, an interphase gap 106 and a second phase 108 being a current square wave of the same magnitude and duration as the first phase 104 but flowing in the opposite direction between an intra-cochlear electrode and (in mono-polar mode) an extra-cochlear electrode. Time periods 110 and 112 are present in which the system generating the stimulations has time to perform any necessary operations in order to configure for the next stimulation. The overall time taken to set-up, deliver and recover from application of a stimulation is one timeslice, in the present example a timeslice is of approximately 69 microseconds duration.

In the present exemplary implementation the preferred maximum stimulation rate is 8 kHz whereas the preferred sampling rate is 16 kHz. Accordingly PERIOD[A] is the number of samples occurring between positive-going zero crossings divided by two and rounded. The PERIOD[A] signal is updated at the end of each period. Thus, the AMP[A], . . . ,AMP[V] and PERIOD[A], . . . , PERIOD[V] signals contain magnitude and period information concerning the ambient sound picked up by microphone 11 for each of the frequency bands monitored by bandpass filters 35.

Next the stimulus signals are selected, as depicted at block 406 of FIG. 4. It is possible to simply stimulate via each corresponding electrode e[i] with a current intensity corresponding to AMP[i] at a time PERIOD[i] into the future in order to convey the information generated by amplitude detectors 37 and period estimators 39 to a wearer of the cochlear prosthesis. For example, with reference to FIGS. 3A, 3B and 3C a stimulation sequence via electrode e[A] is shown corresponding to amplitude and period values generated by amplitude detection module 37A and period estimation module 39 A as shown plotted in FIGS. 3A and 3B. Period[A] is equal to P1 at time t=0 and Amp[A] is equal to a1. Accordingly at a time t=P1 a stimulation current is delivered via electrode e[A] of electrical amplitude I(a1) where I( ) is a loudness growth function which maps amplitude into the dynamic range of the wearer of the prosthesis. This is depicted at block 408 of FIG. 4.

The period P2 and amplitude a2 values are then obtained and a further stimulation is delivered at time t=P1+P2 of amplitude I(a2). This process is repeated continuously to produce the stimulation sequence of biphasic current pulses shown in the graph of FIG. 3C. As previously mentioned, such a process could be simultaneously performed independently on all channels of the implant, (a "channel" as used here refers to a stimulation electrode, its corresponding filter and period and amplitude estimation modules).

In the system thus far described the period estimation module 39A produces a period estimate which is simply the time delay between the last two positive-going zero crossings. While this system works well, any noise on the individual period estimates will degrade the performance of the system. To prevent this, it is desirable to calculate a smoothed period estimate.

The individual period estimates constitute a number sequence which is amenable to any of the methods of smoothing known to the art of digital signal processing. The smoothing may, for example, be implemented as a simple FIR or recursive digital filter—preferably a low-pass filter. Alternatively a rank-order filter, such as a median filter may be used. A rank-order filter has the advantage that it will completely remove any single data errors from the number sequence. A smoothed period estimate is thus produced by applying the sequence of period estimates to a digital filter, and taking the output of that filter. The smoothed period estimate is then utilized by taking the most recent output from the filter and using it in place of the (unsmoothed) period estimate.

Figure 3A:
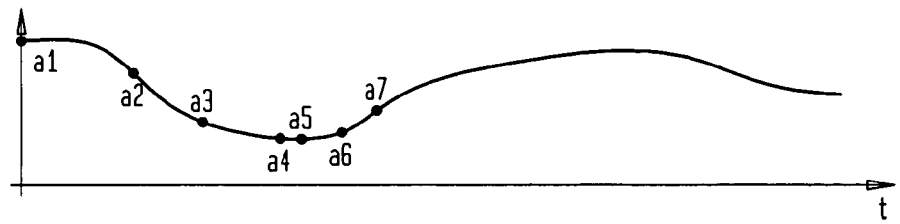
FIG. 3A is a graph of a possible output of an amplitude estimator module of FIG. 2.
Figure 3B:
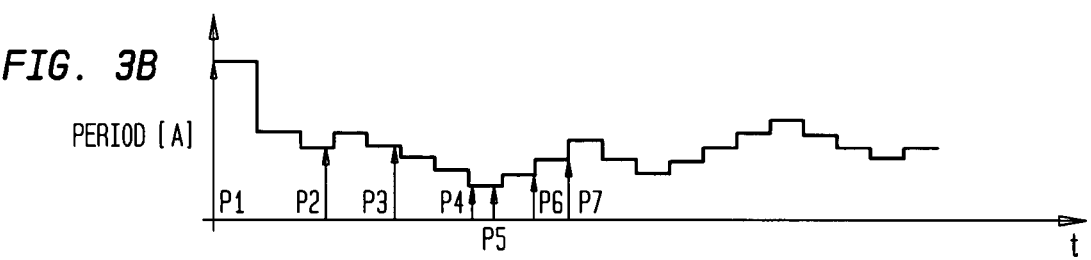
FIG. 3B is a graph of a possible output of a period estimator module of FIG. 2 of the same channel as the amplitude estimator of FIG. 3A.
Figure 3C:
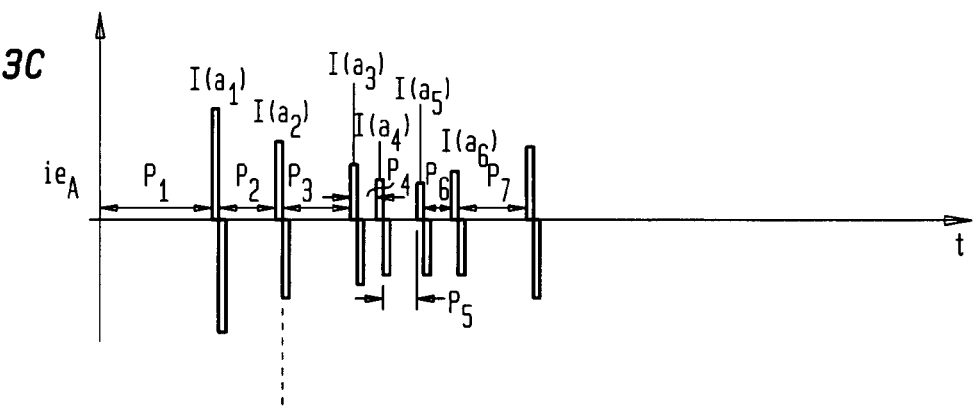
FIG. 3C is a graph of stimulation currents generated via an electrode in accordance with the amplitude and period estimates of FIGS. 3A and 3B.
Figure 3D:
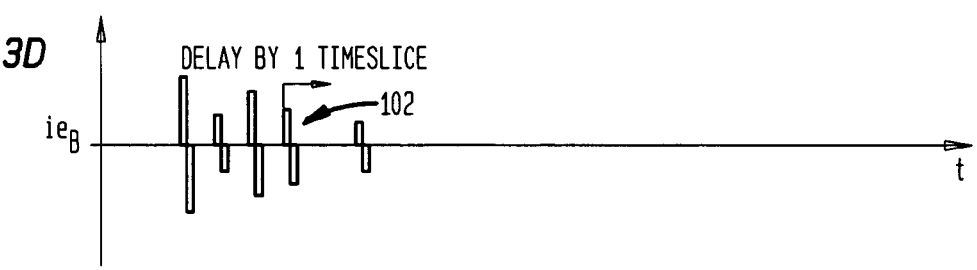
FIG. 3D is a graph of stimulation currents generated via a further electrode having a stimulation current occurring simultaneously with a stimulation current in the graph of FIG. 3C.
Figure 3E:
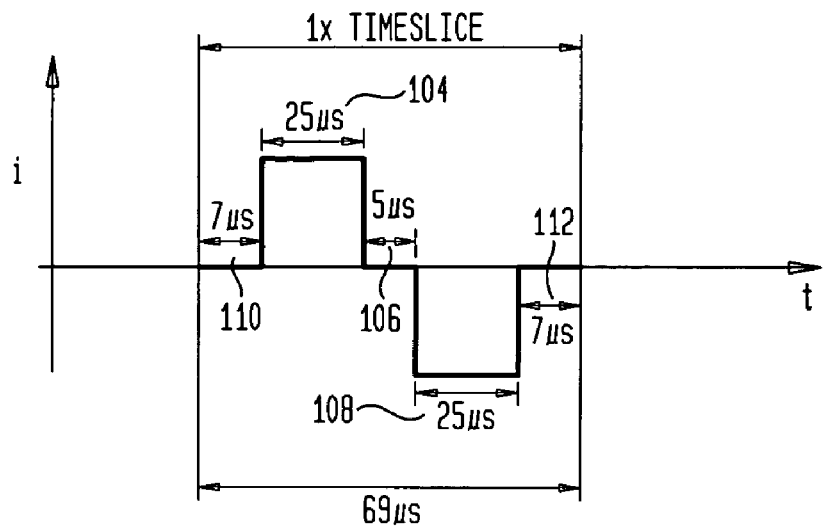
FIG. 3E is a graph of a single stimulation current.

With reference to FIG. 3D there is shown a stimulation sequence via electrode e[B]. It will be noted that stimulation pulse 102 occurs at exactly the same time as stimulation pulse II(a2) of FIG. 3C. Such coincidences occur more and more frequently depending on the number of channels used.

As discussed above, it is well known that simultaneous, or very near simultaneous, stimulation may produce a deterioration in the quality of the sound perceived by the user, due to the interaction of simultaneous current paths between the electrodes.

Figure 5:
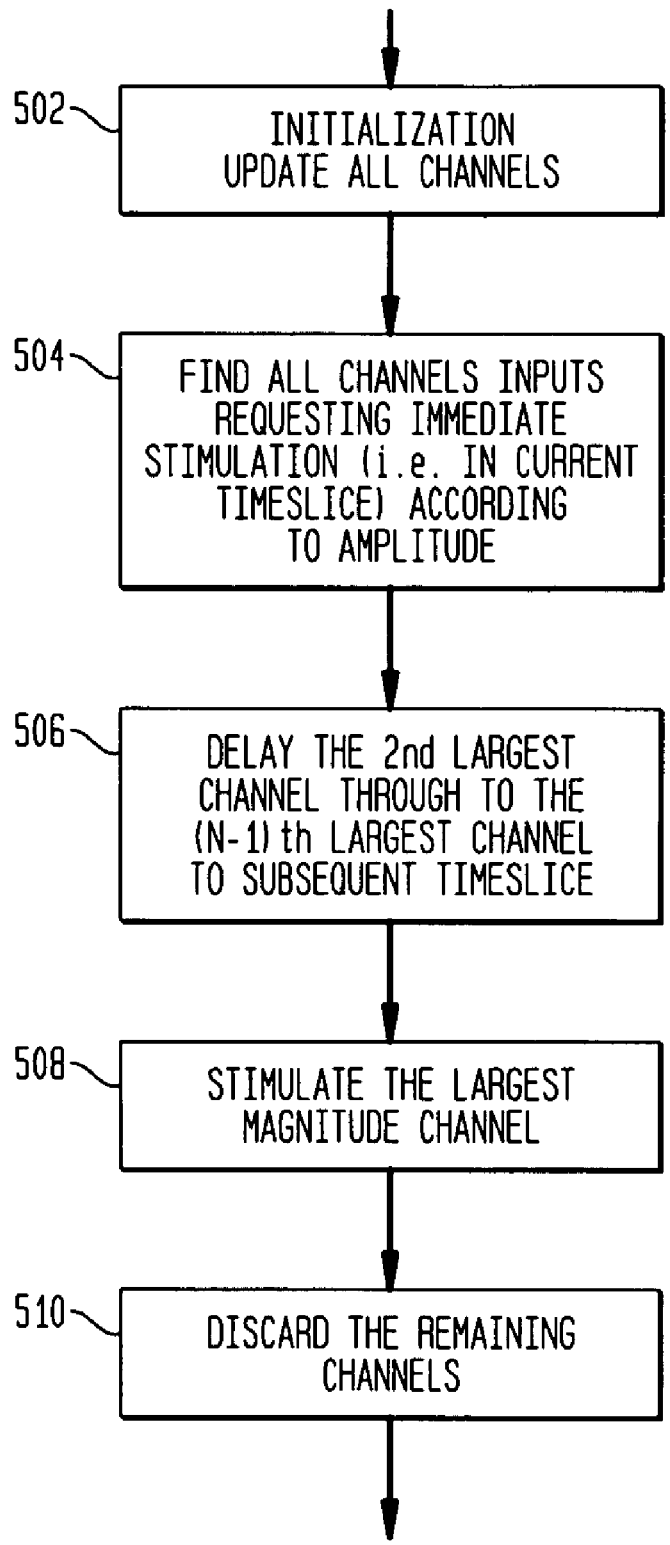
FIG. 5 is a flowchart of procedural sub-steps involved in one of the boxes appearing in FIG. 4.

In light of this issue the inventors have incorporated a refinement for determining which information signals coming from amplitude detectors 37 and period estimation modules 39 are most appropriate to be processed to produce a high quality percept in a user. Referring to FIG. 5, at block 502 the filter channels are updated or initialized. According to certain embodiments of the invention, for any stimulation period, i.e., a "timeslice" such as time slice t0, the signals AMP[A,t0], . . . ,AMP[V,t0] are ordered according to magnitude and a stimulation current is generated by means of the electrode which corresponds to the signal AMP[A,t0], . . . , AMP[V,t0] having the greatest magnitude. (It should be noted that, when implanted, electrodes e[A], . . . ,e[V] are tonotopically mapped to filters fA, . . . ,fV so that electrode e[A] is most apically placed whereas electrode e[v] is most basally placed.) For example, if it is found that AMP[F,t0] has the greatest magnitude at a given timeslice then electrode e[F] is used to deliver the monopolar stimulation in the next timeslice 11. This is depicted at block 504 in FIG. 5.

A further variation to this scheme is that a number of the next largest magnitude signals are also determined in the same timeslice, for example AMP[G,t0]>AMP[B,t0]>AMP [K,t0] might be determined to have the magnitudes next greatest to AMP[F,t0]. In that case those values are assigned to AMP[G,t1], AMP[B,t1] and AMP[K,t1], respectively. During the next timeslice, t1, the procedure is repeated and it may be that AMP[G,t1] is selected as having the greatest magnitude so that electrode e[G] is selected for delivering a stimulation pulse of amplitude corresponding to AMP[G,t1]=AMP [G,t0]. By using this scheme it is possible that signals having a large magnitude, though not the greatest, are presented to the user after a short time delay. This is depicted at block 506 in FIG. 5. The inventors have found that most acoustic power is centered around the lower frequency bands which have longer periods associated with them whereas the higher frequency bands generally have less power associated with them as well as being of shorter period. Accordingly, it is predominantly higher frequency sounds which are delayed rather than lower frequency sounds.

A further refinement is that rather than calculate period estimates with respect of the outputs from filters centered at higher frequencies, for example for filters F1, . . . FV, period estimators 39A, . . . ,39V simply generate a constant signal, or periodicity value. For example, in one embodiment period estimators 39 generate a periodicity value indicating a period of, for example, 1.25 ms, i.e., a periodicity value towards the highest stimulation rate that the device is capable of supporting.

While the preceding description covers a system utilizing period estimators on some or all of the bandpass filtered signals, it is possible to implement the system more simply. For example, in one embodiment a stimulus could be requested each time a positive zero-crossing is detected on a filter output. Once per timeslice each channel is interrogated to see if it has a stimulation request pending. If there are no requests pending, then no action is required. If there is exactly one request pending, then a stimulus is generated corresponding to that request.

If more than one request is pending, then the following actions are taken. The requests are sorted according to the amplitudes of the corresponding bandpass filtered signals (block 504). A stimulus is generated corresponding to the bandpass filtered signal with the largest amplitude (block 506). The next N largest (preferably 5 largest) amplitude requests are delayed by one timeslice (block 508). Any remaining requests are cancelled (block 510).

Referring to FIG. 2, each request generator 41 and its associated period estimation circuit 39 are collectively referred to as pulse requestor 49. Loudness growth function 47 and request arbitrator 43 are collectively referred to as pulse generator 59. The request generators 41A, . . . ,41V and request arbitrator 43 operate to determine which electrode will be stimulated from the AMP[A], . . . ,AMP[V] and PERIOD[A], . . . ,PERIOD[V] signals. The operation of the request generators and the request arbitrator, in order to implement the above scheme, will now be explained with exemplary reference to request generator 41A.

The AMP[A] and PERIOD [A] signals are inputs to request generator module 41A. Another input to the request generator is the CLK signal which corresponds to the present timeslice. The CLK signal is modulus 256 to avoid overflow problems.

Another input to request generator 41A is a command signal ARB_CMD[A] from request arbitrator 43.

The outputs from request generator 41A are TSLICE[A] and REQ_AMP[A].

The TSLICE[A] represents the time at which it is proposed by generator 41A that a stimulation be delivered having an amplitude value represented by REQ_AMP[A].

The relationship between TSLICE[A] and PERIOD[A] and REQ_AMP(A) and AMP[A] is determined by the value of the ARB_CMD[A] signal. The ARB_CMD[A] signal can take one of three values REQUEST, DELAY, DISCARD. When ARB_CMD[A] takes the value:

REQUEST then REQ_AMP[$A$]:=AMP[$A$]; TSLICE[$A$]:=CLK+ PERIOD[$A$]

DELAY then TSLICE[$A$]:=TSLICE($A$)+1

DISCARD take no action.

The principle behind these rules is that in the event that request arbitrator 43, whose operation will shortly be described, determines that a stimulation pulse should be applied corresponding to the output from filter 35 A then by sending an ARB_CMD[A] signal having the value REQUEST to request generator 41A the amplitude and timing of the stimulation pulse is made available at the next timeslice. Alternatively, if ARB_CMD[A] takes the value DELAY then the corresponding TSLICE[A] variable is incremented. Construction of the request generator, in order to implement the above rules is readily accomplished according to established synchronous digital design techniques.

Request arbitrator module 43 takes as its input the signals TSLICE[A], . . . , TSLICE[V] from each of the request generators 41A-41V, REQ_AMP[A], . . . ,REQ_AMP[V] and the CLK signal. Arbitrator module 43 generates a signal P_CHAN which identifies which of electrodes e[A], . . . ,e[V] of the electrode array is to be used to apply a stimulation.

The arbitrator module also generates a signal P_AMP which takes a value REQ_AMP[A], . . . ,REQ AMP[V] which is used, after scaling as will subsequently be described, to determine the amplitude of the signal to be used when applying stimulation. Request arbitrator module 43 operates according to the following rules:

1. Find all TSLICE[i] with a value equal to CLK.
2. Find N channels of those determined in Step 1 which have the largest value of REQ_AMP[j]. The channel with the largest value of REQ_AMP[j] and TSLICE[j] as determined in step 1 is found and P_CHAN set to j and P_AMP set to REQ_AMP[j]. So that a stimulation is directed via electrode e[j] with amplitude scaled from the value P_AMP=REQ_AMP[j]. This is accomplished by setting the ARB_CMD[j] signal to REQUEST.
3. The channels having the next N−1 largest amplitude values REQ_AMP[ ] are delayed by one timeslice for consideration during set up for the next stimulation. This is achieved by sending an ARB_CMD[ ] signal to the corresponding N−1 request generators to DELAY.
4. The remaining channels, which were selected in step 1 but not in step 2 are discarded. This is achieved by sending the corresponding request generators an ARB_ CMD[ ] signal of value DISCARD.
5. If any of the request generators is sending a specific "no pulse request" then the corresponding ARB_CMD[ ] signals are set to REQUEST.

Once the P_CHAN and P_AMP values have been determined they are passed to Loudness Growth Function (LGF) module 47. As noted above with reference to block 408, the growth function module takes into account the predetermined comfort and threshold levels of the user of the cochlear prosthesis in order to map 50 the P_AMP values into the listener's dynamic range. Such mapping is known in the prior art and the reader is referred to U.S. Pat. No. 4,532,930 for further details.

The invention is most conveniently practiced, in accordance with the embodiment of FIG. 1A, by programming a SPrint speech processor, available from Cochlear Limited of 14 Mars Road, Lane Cove, NSW 2066, Australia, in order to perform the operations described herein. In one application, the SPrint speech processor is used in conjunction with a C124M cochlear implant receiver-stimulator from the same vendor.

At block 402, for each sample period, the sound signal is filtered into the required number of channels. At block 404, the signal in each channel is analyzed to determine its amplitude, and the period of the signal. The latter may be performed by determining the time between successive zero crossings, as described above. Based upon the values for the amplitude and period for each channel, at block 406 the channel signal is to be used as the basis for stimulation, and hence the electrode to be stimulated, is selected. Loudness mapping block 408 performs the function of mapping the desired amplitude stimulus within the dynamic range for the selected electrode. The latter step is well known to those skilled in the art.

FIG. 5 illustrates one embodiment of the operational steps performed at block 406 of FIG. 4. At initialization, in block 502, the stimulus selector updates all inputs. The inputs are the values for amplitude and period as described previously. At block 504, each input channel is checked to determine if a stimulation is being requested for the next period, based upon the period value, and all such channels are sorted according to amplitude. At block 506, all channels but the largest amplitude channel are delayed to a later stimulation period. At block 508, the largest amplitude channel is selected as the basis for stimulation, and the inputs for that channel are updated to reflect that a stimulus will be delivered that period. Block 510 completes the process by discarding the remaining channels by updating their inputs. The operations illustrated in FIG. 5 are repeated for each period.

This application is a divisional application of U.S. patent application Ser. No. 10/030,830, filed Jun. 5, 2002, which is a national stage application of PCT/AU 2000/000838 filed Jul. 12, 2000, which claims priority from Australian Provisional Application PQ 1610 filed Jul. 13, 1999. The entire disclosure and contents of the above applications are hereby incorporated by reference herein.

While the invention has been described with reference to preferred embodiments, it is to be understood that these are merely illustrative of the application of principles of the invention. Accordingly, the embodiments described in particular should be considered exemplary, not limiting, with respect to the following claims.

The invention claimed is:

1. A cochlear implant prosthesis for delivering to a recipient's cochlea stimulation pulses representing a received audio signal, comprising:
    a processor configured to process electrical signals corresponding to the received audio signal to produce a plurality of filtered signals having different center frequencies;
    a plurality of amplitude detectors each configured to produce a magnitude signal dependent on the magnitude of one of said filtered signals;
    a plurality of pulse requestors each configured to produce a pulse request signal dependent on a periodicity of one of said filtered signals;
    a pulse generator configured to produce stimulation pulses at time instants dependent on said pulse request signals, with the magnitude of said stimulation pulses dependent on said magnitude signals; and
    a plurality of electrodes for delivering said stimulation pulses to the recipient's cochlea.

2. The cochlear implant prosthesis of claim 1, wherein one or more of said plurality of pulse requesters are responsive to a filtered signal having a high center frequency, and further wherein said one or more pulse requesters each produce said pulse request signals with a constant time interval.

3. The cochlear implant prosthesis of claim 1, wherein each said pulse requestor comprises:
    a period estimator configured to determine a period of said filtered signal.

4. The cochlear implant prosthesis of claim 3, wherein each said period estimator is configured to measure a time interval between successive positive zero-crossings of said filtered signal.

5. The cochlear implant prosthesis of claim 3, wherein each said period estimator is configured to measure a time interval between successive positive zero-crossings of said filtered signal, and further wherein said pulse requestor further comprises:
    a request generator configured to generate said pulse request signal in response to said time intervals.

6. The cochlear implant prosthesis of claim 5, wherein said request generator is further responsive to previous values of said time interval so as to generate said pulse request signal in response to a smoothed time interval value.

7. The cochlear implant prosthesis of claim 1, wherein each said pulse requestor is configured to generate a pulse request signal each time a positive zero-crossing is detected on said filtered signal.

8. The cochlear implant prosthesis of claim 1, wherein said pulse generator comprises:
    a pulse request arbitrator configured to receive said pulse request signals from said plurality of pulse requestors, wherein said pulse request arbitrator is further configured to permit a single pulse to be generated at a given time.

9. The cochlear implant prosthesis of claim 8, wherein when a plurality of pulse requestors simultaneously produce a pulse request signal, said single pulse permitted by said pulse request arbitrator is a pulse which has a greatest corresponding magnitude signal.

10. The cochlear implant prosthesis of claim 8, wherein said pulse request arbitrator is further configured to examine said pulse request signals at a start of each timeslice, wherein said timeslice is the time taken to output a stimulation pulse.

11. The cochlear implant prosthesis of claim 10, wherein said pulse request arbitrator is further configured to wait until a next timeslice when no pulse request signals are produced by said plurality of pulse requestors.

12. The cochlear implant prosthesis of claim 10, wherein said pulse request arbitrator is further configured to order according to magnitude said magnitude signals corresponding to the active pulse request signals, and to produce a stimulation pulse corresponding to a greatest magnitude signal, and delay by one timeslice a number of said pulse request signals corresponding to a next greatest magnitude signals, and to discard any remaining pulse request signals.

13. The cochlear implant prosthesis of claim 1, wherein said pulse generator is further configured to permit a plurality of pulses to be generated simultaneously when a plurality of pulse request signals are simultaneously active.

14. A method for delivering to a recipient's cochlea stimulation pulses representing a received audio signal, comprising:

processing electrical signals corresponding to the received audio signal to produce a plurality of filtered signals having different center frequencies;

producing a plurality of magnitude signals each representative of the magnitude of one of said plurality of filtered signals;

producing one or more pulse request signals each depending on a periodicity of one of said plurality of filtered signals;

producing stimulation pulses at time instants dependent on said one or more pulse request signals, with a magnitude of said stimulation pulses dependent on said magnitude signals; and delivering said stimulation pulses to the recipient's cochlea.

15. The method of claim 14, wherein said producing one or more pulse request signals comprises:

producing one or more pulse request signals responsive to a filtered signal having a high center frequency, wherein said one or more pulse request signals have a constant time interval.

16. The method of claim 14, wherein said producing one or more pulse request signals comprises:

measuring a time interval between successive positive zero-crossings of said plurality of filtered signals.

17. The method of claim 16, wherein said producing one or more pulse request signals comprises:

generating a pulse request signal each time a positive zero-crossing is detected on said filtered signal.

18. The method of claim 16, wherein said producing one or more pulse request signals comprises:

producing one or more pulse request signals based on a time interval between successive positive zero-crossings of said plurality of filtered signals.

19. The method of claim 14, wherein said producing stimulation pulses comprises:

producing a single stimulation pulse at a given time.

20. The method of claim 19, wherein producing said single stimulation pulse comprises:

producing a single stimulation pulse which has the greatest corresponding magnitude signal.

21. The method of claim 14, wherein said producing stimulation pulses comprises:

producing a plurality of stimulation pulses simultaneously when a plurality of pulse request signals are simultaneously active.

22. The method of claim 14, wherein said producing one or more pulse request signals comprises:

examining said pulse request signals at a start of each timeslice, wherein said timeslice is the time taken to output a stimulation pulse.

23. The method of claim 22, wherein said producing one or more pulse request signals comprises:

waiting until a next timeslice when no pulse request signals are produced.

24. The method of claim 14, wherein said producing one or more pulse request signals comprises:

ordering according to magnitude said magnitude signals corresponding to the active pulse request signals;

producing a stimulation pulse corresponding to a greatest magnitude signal;

delaying by one timeslice a number of said pulse request signals corresponding to a next greatest magnitude signals, and to discard any remaining pulse request signals.

* * * * *